United States Patent

Warren et al.

[11] Patent Number: 5,432,085
[45] Date of Patent: Jul. 11, 1995

[54] CELL FEEDER/HARVESTER ASSEMBLY

[76] Inventors: Richard J. Warren, 7245 SW. 87th Ave., Ste. 100, Miami, Fla. 33173; Maher M. Lewis, 6035 SW. 127 Pl., Miami, Fla. 33183; Kitchener C. Wilson, 415 Calle La Caleras, Santa Barbara, Calif. 93209

[21] Appl. No.: 96,789

[22] Filed: Jul. 23, 1993

Related U.S. Application Data

[63] Continuation-in-part of Ser. No. 973,911, Nov. 10, 1992, abandoned.

[51] Int. Cl.⁶ .............................................. C12M 1/32
[52] U.S. Cl. .................................. 435/289; 435/293; 435/298; 435/809; 422/100
[58] Field of Search ................. 435/3, 30, 29, 40, 287, 435/289, 292, 293, 296–298, 299–301, 311, 809; 422/63–66, 99, 100–102, 104; 73/863.01, 863.81, 863.28, 863.81, 863.91; 53/109, 381.4

[56] References Cited

U.S. PATENT DOCUMENTS

| | | | |
|---|---|---|---|
| 3,772,154 | 11/1973 | Isenberg et al. | 435/30 |
| 4,090,921 | 5/1978 | Sawamura et al. | 435/289 |
| 4,494,363 | 1/1985 | Rica et al. | 53/381.4 |
| 4,495,149 | 1/1985 | Iwata et al. | 422/65 |
| 4,812,392 | 3/1989 | Miyake et al. | 422/65 |
| 4,873,875 | 10/1989 | Cork | 73/863.01 |
| 5,055,263 | 10/1991 | Meltzer | 422/100 |
| 5,108,703 | 4/1992 | Pfost et al. | 422/65 |

Primary Examiner—William H. Beisner
Attorney, Agent, or Firm—Robert M. Downey

[57] ABSTRACT

A cell feeder/harvester assembly including a primary platform with at least one recessed culture vessel holding area whereon two pipet tip racks, one for holding sterile pipet tips and the other rack for collecting used pipet tips, and an array of culture vessels are supported. An X assembly extends transversely across the primary platform and is driven longitudinally thereover, the X assembly having a Y assembly, including a secondary platform, disposed thereon which is adapted to be driven transversely over the X assembly, wherein both the X assembly and the Y assembly move so as to position a Z assembly, which is attached to a top of the secondary platform, over a select pair of culture vessels on opposite sides of the secondary platform. The Z assembly is adapted to service all culture vessels on the primary platform, without the need for manual or individualized directing, by removing waste products and adding necessary chemicals to the individual culture vessels. The Z assembly includes a cover remover and nurturing assembly which is adapted to remove the cover from the culture vessel which is being serviced and subsequently distribute chemicals to the uncovered culture vessel, via a sterile pipet tip. After servicing the particular culture vessel, the used pipet tip is disposed of in the collecting rack and a new, sterile pipet tip is replaced on the nurturing assembly. The functioning of the servicing procedures being completely computer controlled such that all culture vessels are given their necessary specialized servicing.

13 Claims, 3 Drawing Sheets

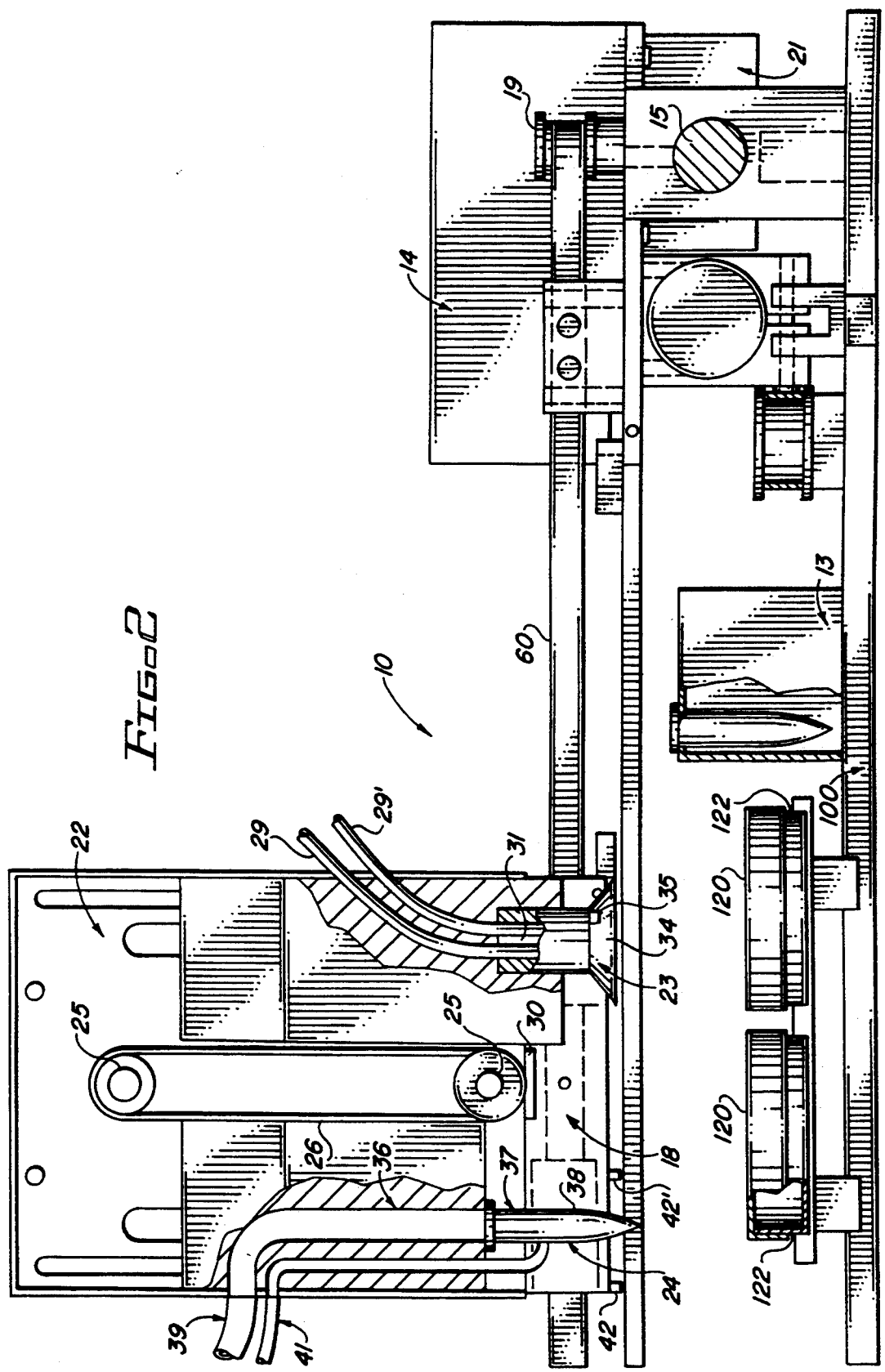

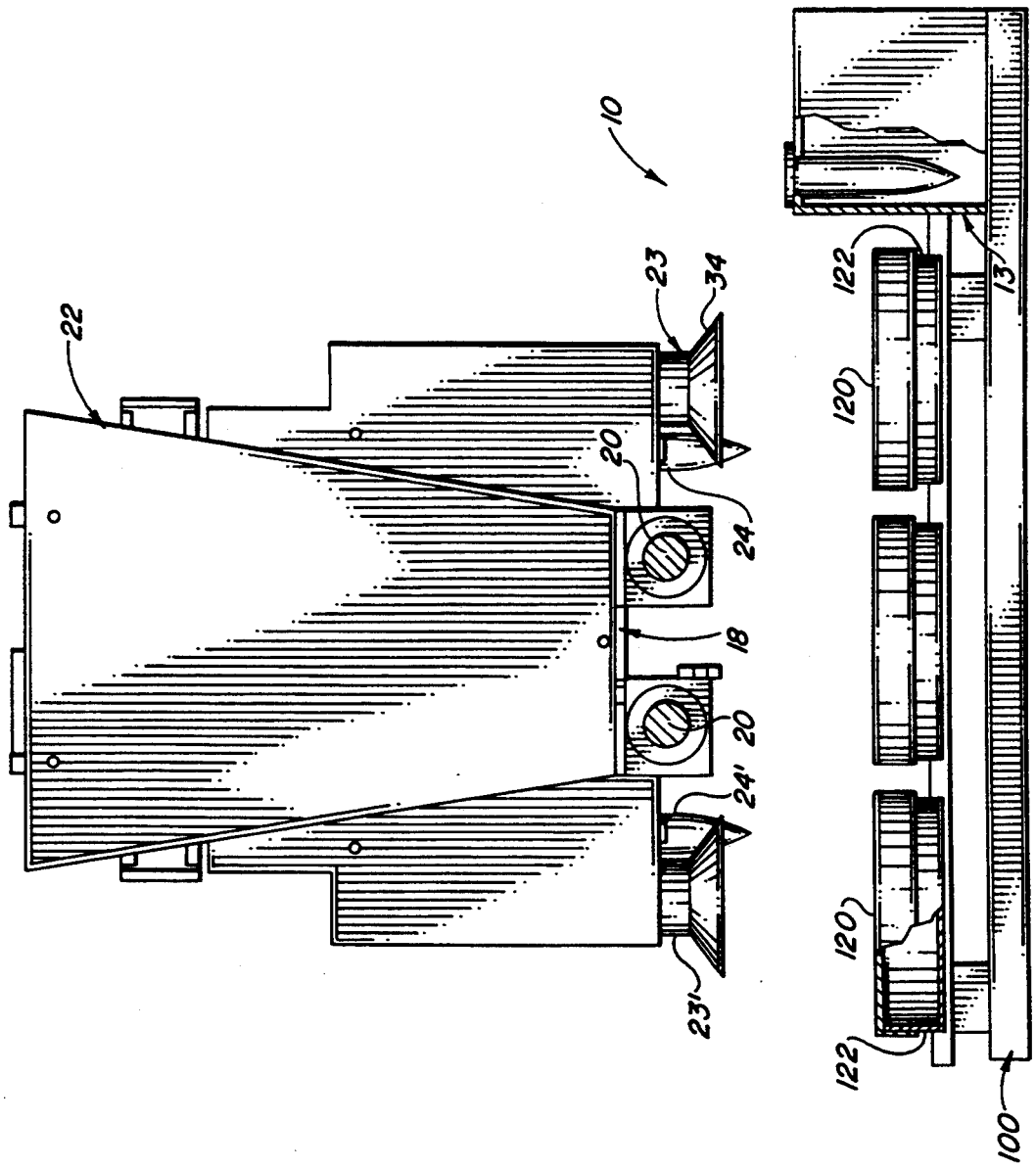

CELL FEEDER/HARVESTER ASSEMBLY

BACKGROUND OF THE INVENTION

This application is a continuation-in-part application of the previously filed patent application Ser. No. 973,911 filed on Nov.10, 1992 now abandoned.

FIELD OF THE INVENTION

This invention relates to an automated feeder/harvester assembly adapted to remove waste and provide necessary nutrient chemicals for cell cultures in a controlled environment.

DESCRIPTION OF THE RELATED ART

The process of growing cell cultures is highly specific requiring that the environmental conditions in which the cell is kept aseptic, constant and precise. It is important that specialized care procedures relating to removing waste created by the cell and adding appropriate nutrient and other chemicals to further the growth of the cell be followed, protecting both the culture and the technician. Once growth is successful, the culture must further be harvested by precise and controlled procedures necessitating specific quantities of the harvesting chemicals. Traditionally, the care procedures for such cell cultures have been undertaken in an environmentally controlled work space and have been manually performed. These procedures, however, may lead to many difficulties if contaminants are introduced by a human technician, if measurements are not precisely made by the technician, or if the technician is exposed to a pathogen contained in the culture. Even with the most careful and accurate human technician, naturally human error is always possible in the measurement of dosages, which tend to be small, precise quantities, in the timing of dosages, which must often be administered at precise times, or in the complete elimination of contaminants. It is also very possible to accidentally introduce contaminants. Although there exists environmentally controlled work spaces which enable individuals outside the work space to work within the environmentally controlled area, the working conditions are often cumbersome and do not eliminate the difficulties associated with manual care. Further, despite the presence of numerous automated laboratory devices, none are specifically adapted to care for numerous specimens, providing each specimen with the specific aseptic care necessitated by it. Therefore, in this highly specialized field, it would be most beneficial to provide an assembly which is specifically adapted for the care and attendance to numerous growing cells, while providing each with the specific care it requires and assuring that the growth environment of the particular cell is aseptically maintained at the appropriate levels without the introduction of outside contaminants, or without risking exposure of the human technician to pathogens. The assembly of the present invention is designed specifically to meet these needs and is precisely adapted to both cleanse and provide nutrients for growing cells, and to ultimately harvest the mature culture, while protecting the technician.

SUMMARY OF THE INVENTION

The present invention is directed towards a cell feeder/harvester assembly adapted to aseptically care for and harvest cells, which are contained within culture vessels, during their growth. The feeder/harvester assembly includes a primary platform having at least one recessed culture vessel holding area disposed therein, wherein at least one culture vessel is supported. Further, the primary platform includes at least one pipet tray holding recess wherein at least one pipet tray is supported. Positioned within the pipet tray are a plurality of sterile pipet tips, disposed vertically therein for facilitated use. A similar pipet tray, devoid of any pipet tips, is supported in a recessed area of the primary platform to receive used pipet tips. Extending transversely across the primary platform is an X assembly. The X assembly is structured and disposed to move longitudinally over the primary platform and is moved predetermined longitudinal distances over the primary platform by a computer controlled longitudinal drive means. Disposed atop this X assembly is a Y assembly. The Y assembly is adapted to move transversely on the X assembly and is driven predetermined transverse distances over the X assembly by computer controlled transverse drive means. Further, the Y assembly includes a secondary platform mounted thereon. Disposed atop this secondary platform is a Z assembly. The Z assembly is structured and disposed to service a corresponding pair of the culture vessels simultaneously and includes a pair of oppositely disposed cover removers and a pair of oppositely disposed nurturing assemblies. Each of the pair of oppositely disposed cover removers is correspondingly disposed adjacent one of the pair of oppositely disposed nurturing assemblies such that a first side of the secondary platform is overhung by a first cover remover and nurturing assembly unit and a second side of the secondary platform is overhung by a second cover remover and nurturing assembly unit. Accordingly, the pair of culture vessels to be serviced simultaneously will be corresponding disposed beneath the first and second side of the secondary platform. In order to raise and lower the cover removers and the nurturing assemblies predetermined vertical distances during servicing of the culture vessels, the Z assembly includes computer controlled vertical drive means. Each of the cover removers of the Z assembly includes a lower surface structured and disposed to contact and hold a cover of one of the culture vessels until replacement thereof on the culture vessel, both cover removers functioning simultaneously. In order to facilitate holding of one of the covers by the cover remover, each cover remover includes a suction tube extending therethrough to its lower surface on which is attached a suction cup. The suction tube is specifically structured and disposed to provide sufficient suction at the lower surface of the cover remover so as to remove and hold the cover of the culture vessel while the culture vessel is being serviced. So as to properly detect that successful attachment of the lower surface of the cover remover and the cover of the culture vessels has been achieved, each of the cover removers includes a vacuum sensor. The vacuum sensors function such that unless both cover removers are properly holding a corresponding cover, the servicing procedures may not continue. Disposed within each of the nurturing assemblies is a central conduit. Further, each of the nurturing assemblies includes a pick-up nipple protruding from a lower surface thereof, the pick-up nipple being adapted to be inserted into one of the pipet tips in the pipet tray, both pick-up nipples functioning simultaneously. In order to secure the pipet tip to the pick-up nipple, each pick-up nipple is interconnected to vacuum means adapted to provide sufficient suction at the pick-up nipple for holding the pipet tip. Additionally, means to detect the attachment of one of the pipet tips to each of the pick-up nipples is included so as to assure that both pick-up nipples include sterile pipet tips secured thereto before servicing may continue. Each of the pipet tips enters one of the uncovered culture vessels upon downward motion of the nurturing assembly, through a predetermined vertical distance controlled by a computer. So as to provide proper servicing, each of the nurturing assemblies includes suction means interconnected to the vacuum means and structured and disposed to remove waste from one of the uncovered culture vessels through the sterile pipet tips. Further, each of the nurturing assemblies includes chemical distributing means structured and disposed to insert necessary chemicals into the uncovered culture vessel. The functioning of the feeder/harvester assembly is directed by computer control means which specifically orders the position of the Z assembly with regard to the culture vessels located on the primary platform, thereby assuring that all of the culture vessels in the recessed culture vessel holding area will be properly serviced by the assembly.

It is an object of the present invention to provide a cell feeder/harvester assembly which is highly precise and requires no manual controlling.

Yet another object of the present invention is to provide a cell feeder/harvester assembly which does not require constant manual attention in order to properly care for cells being grown.

Still another object of the present invention is to provide a cell feeder/harvester assembly which will limit the possibility of introducing outside contaminants to a cell's growth environment yet will enable proper and complete care to be provided for the cell.

A further object of the present invention is to provide a cell feeder/harvester assembly which will enable a large number of cells to be properly and precisely cared for in an efficient manner.

Yet another object of the present invention is to limit the possibility of infecting an operator/technician from exposure to an infected culture, for example a culture infected with a virus such as HIV.

BRIEF DESCRIPTION OF THE DRAWINGS

For a fuller understanding of the nature of the present invention, reference should be had to the following detailed description taken in connection with the accompanying drawings in which:

FIG. 2 is a side elevation view of the cell feeder/harvester assembly.

FIG. 3 is a partial front elevational view of the cell feeder/harvester assembly illustrating a dual Z head assembly and culture vessel holding area of the present invention.

DETAILED DESCRIPTION OF THE PREFERRED EMBODIMENT

Figure 1:
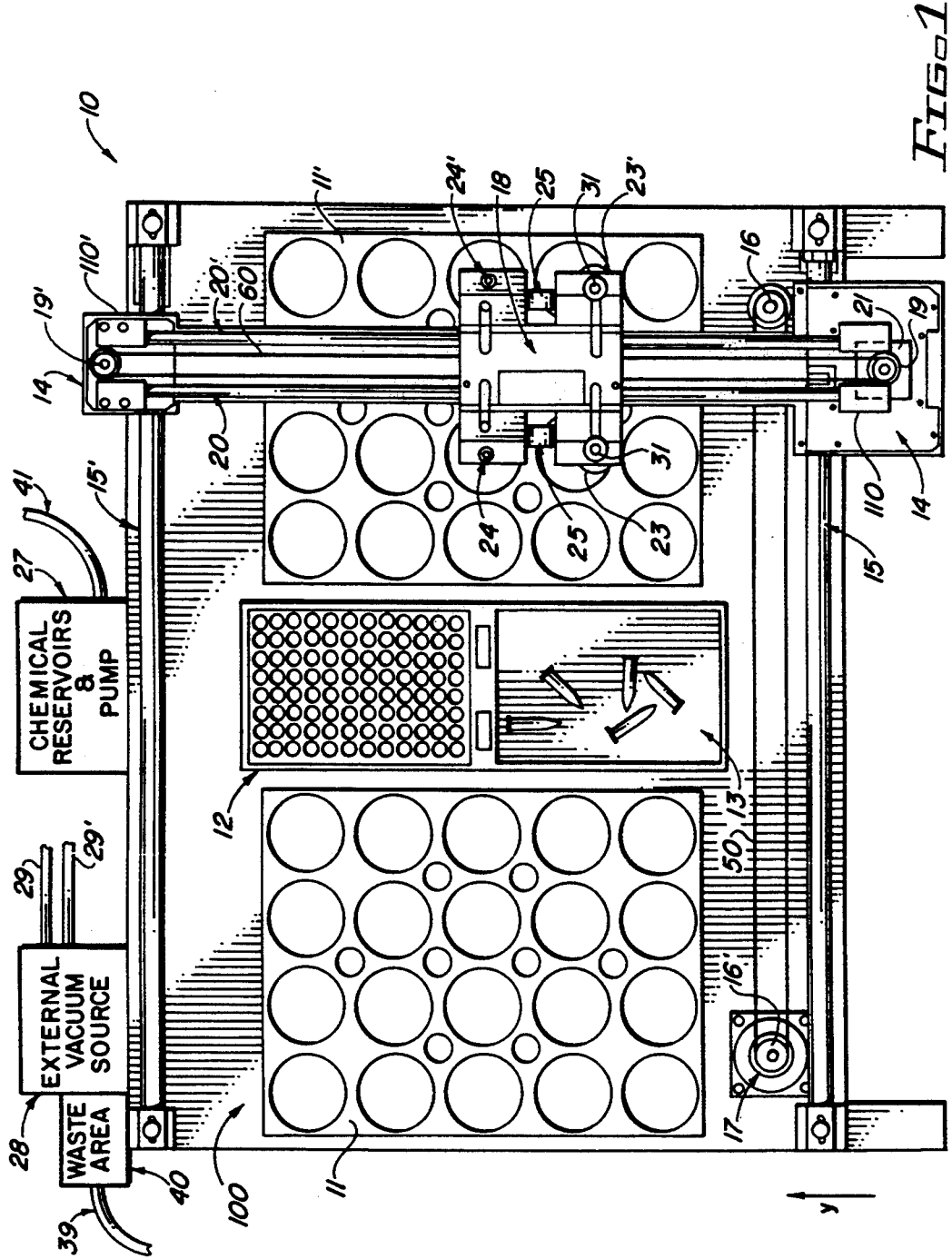
FIG. 1 is a top plan view of the cell feeder/harvester assembly of the present invention.

Shown throughout the figures, the present invention is directed towards a cell feeder/harvester assembly, generally indicated as 10. The feeder/harvester assembly 10 includes a primary platform 100 having a pair of spaced, recessed culture vessel holding areas 11, 11'. Each of the recessed culture vessel holding areas is adapted to hold one or a plurality of culture vessels, each containing a cell culture to be grown therein. As illustrated, a culture vessel holding tray having a number of sized openings adapted to hold a single culture vessel may be utilized and fitted into the recessed culture vessel holding areas. Further disposed within the primary platform and centrally disposed between the pair of spaced culture vessel holding areas, are a sterile pipet tray holding recess 12 and a pipet disposal tray recess 13. The sterile pipet tray holding recess is adapted to hold therein a pipet tray wherein a plurality of sterile pipet tips are vertically positioned. The sterile pipet tips are vertically positioned with their wider mouth portion protruding from the pipet holding tray. The pipet disposal recess contains an empty pipet tray wherein used pipet tips may be discarded. Movable along a length of the primary platform and extending transversely thereacross is an X assembly 14. The X assembly is adapted to move longitudinally along the primary platform. In order to slidably hold the X assembly over the primary platform, a first pair of rails 15, 15' extend longitudinally along opposite sides of the primary platform. As shown, these first pair of rails may either rest atop the primary platform or overhang the primary platform and be secured to support stanchions thereof. Disposed adjacent opposite distal ends of one of the first pair of elongate rails are a first pair of pulleys 16, 16'. These first pair of pulleys are included as part of computer controlled longitudinal drive means adapted to move the X assembly predetermined longitudinal distances over the primary platform on the first pair of rails. Drivingly engaged about the first pair of pulleys is a first drive belt 50. This first drive belt 50 is secured to the carrier assembly by a drive clamp, such that movement of the first drive belt will result in corresponding longitudinal movement of the X assembly. Movement of the drive belt 50 is accomplished by a first step motor 17 mounted to the primary platform and engaged in driving relation with one of the first pair of pulleys, 16', thereby rotating the first pair of pulleys and resulting in the corresponding movement of the drive belt 50 and X assembly 14.

The X assembly, which moves over the primary platform, 100, includes a pair of oppositely disposed mounting members 110, 110' which are mounted on the first pair of rails. Spanning these mounting members 110, 110' of the X assembly are a second pair of elongate rails 20, 20'. Slidably mounted along this second pair of elongate rails is a Y assembly 18. This Y assembly includes a secondary platform adapted to move transversely over the primary platform as a result of computer controlled drive means on the X assembly. These computer controlled transverse drive means of the X assembly include a second pair of pulleys 19, 19' disposed adjacent to one of the second pair of rails. As illustrated, the second pair of pulleys may also be effectively mounted on the mounting members in a position between the second pair of rails. Drivingly engaged about this second pair of pulleys is a second drive belt 60. The second drive belt 60 is adapted to move in accordance with the movement of the second pair of pulleys 19, 19' and is secured to the secondary platform of the Y assembly 18 such that movement of the second drive belt 60 results in corresponding movement of the Y assembly 18. A second step motor 21 is disposed at one of the mounting members so as to drive the second pair of pulleys 19, 19' and accordingly move the second drive belt 60 and the Y assembly 18. By moving the X assembly 14 longitudinally over the primary platform 100, and by moving the Y assembly 18 transversely over the primary platform 100, the secondary platform may be disposed in any location over the primary platform 100 as needed, thereby enabling all culture vessels and pipet tips contained in the recessed holding areas on the primary platform 100 to be accessible.

Disposed atop the secondary platform of the Y assembly is a Z assembly 22. This Z assembly 22 is positioned so as to generally overhang a first and a second side of the secondary platform thereby being accessible to engage pipet tips and/or a pair of culture vessels within the respective holding areas. Due to the size of the secondary platform, the Z assembly is adapted specifically to service culture vessels in alternating rows, thereby resulting in one row of culture vessels being disposed directly beneath the secondary platform, with the alternating rows being disposed in serviceable orientation directly beneath the first and second sides of the secondary platform. This Z assembly 22 includes primarily a pair of oppositely disposed cover removers 23, 23' and a pair of oppositely disposed nurturing assemblies 24, 24'. Each of the pair of oppositely disposed cover removers 23, 23' is correspondingly disposed adjacent to one of the pair of oppositely disposed nurturing assemblies 24, 24' thereby forming a first cover remover and nurturing assembly unit overhanging the first side of the secondary platform, and a second cover remover and nurturing assembly unit overhanging the second side of the secondary platform, each cover remover and nurturing assembly unit being adapted to simultaneously service a corresponding culture vessel. The cover removers 23, 23' and nurturing assemblies 24, 24' are adapted to be raised and lowered predetermined vertical distances by computer controlled vertical drive means, thereby properly engaging the culture vessels within one of the recessed culture vessel holding areas. The computer controlled vertical drive means is defined by a third and fourth pair of pulleys 25, 25' each pair being disposed between the cover remover 23, 23' and nurturing assembly 24, 24' of a corresponding one of the first and second units. The third and fourth pair of pulleys 25, 25' each have a third and fourth drive belt 26, 26' drivingly engaged thereabout. These third and fourth drive belts 26, 26' are each correspondingly attached to both the cover remover 23, 23' and nurturing assembly 24, 24' of either the first or second unit such that movement of the third and fourth drive belts 26, 26' as a result of a third step motor 30 rotating the third and fourth pair of pulleys 25, 25', will result in corresponding vertical movement of the cover removers 23, 23' and nurturing assemblies 24, 24'. In the preferred embodiment, the movement of each cover remover is linked to its corresponding nurturing assembly such that when each cover remover is lowered, the corresponding nurturing assembly is simultaneously raised and vice versa. So as to guarantee proper guided vertical movement of the cover removers and nurturing assemblies, the assembly includes a plurality of vertically oriented drive slots.

Each of the cover removers 23, 23' is adapted to remove the cover 120 from a culture vessel 122 by means of an external vacuum source 28 connected to the cover remover via conduits 29, 29' providing suction which lifts the cover 120 from the culture vessel 122 and holds it leaving the culture vessel 122 uncovered such that it may be serviced by the nurturing assembly. The conduits extending from the vacuum source interconnect with a suction tube 31 extending through the cover remover. The suction tube passes through the cover remover to a suction cup 34 disposed at a lower surface of the cover remover at which point sufficient suction is created to remove the cover 120 from the culture vessel 122. In order to detect that successful attachment of the cover of the culture vessel to the suction cup 34 of the cover remover 23 has been achieved, the cover remover includes a vacuum sensor 35 structured and disposed to detect secure, air tight attachment between the cover and lower surface of the suction cup 34. The vacuum sensors, which are included in each of the cover removers, are specifically adapted to assure that both of the cover removers 23, 23' have properly attached a corresponding cover 120 before further servicing of culture vessels may proceed. Subsequent to engagement by the cover removers with the covers of the culture vessels, the cover removers are raised and the Z assembly is moved transversely over the primary platform 100 such that the nurturing assemblies directly overlie the uncovered culture vessels and proper servicing thereof can commence. Each of the nurturing assemblies includes a central conduit, 36, extending to a lower surface thereof. Further included as part of each nurturing assembly is a pick-up nipple, 37, protruding from the lower surface. Each of the pick-up nipples is structured and disposed to be inserted into a corresponding pipet tip, 38, in the pipet holding tray for engagement therewith. The pipet tips within the holding tray are sterile and prior to commencing servicing on any pair of culture vessels, the Z assembly is positioned over the pipet holding tray such that each of the pick-up nipples of the nurturing assembly of the Z assembly can pick up sterile pipet tips. The external vacuum source, 28, is further interconnected to the pick-up nipple of each of the nurturing assemblies which enables the pipet tip to be secured to the pick-up nipple by suction. In order to be certain that both of the pick-up nipples have properly secured sterile pipet tips, infra red beam sensors 42, 42' are included wherethrough the pipet tips on the pick-up nipples are passed. If both of the pick-up nipples are detected to have a pipet tip secured thereto, servicing will continue, if not, the procedure is ceased until both pick-up nipples are properly fitted with sterile pipet tips. The central conduit within each of the nurturing assemblies, extends away from the pick-up nipple and sterile pipet, each including a central opening. The external vacuum source, 28, connected to the nurturing assembly creates significant suction through the suction conduit, 39, and central conduit, 36, such that upon lowering of the sterile pipet tip into the uncovered culture vessel, waste within the uncovered culture vessel is removed and discarded in a waste disposal area, 40. The chemical dispersion conduits, 41, of each of the nurturing assemblies come together at a junction where they are connected to a single chemical reservoir. The chemical dispersion conduit is attached to a pump, 27, whereby the necessary and precise quantities of chemicals are directed through the chemical dispersion conduits for release into the uncovered culture vessel. The chemical reservoir can either be a single reservoir or, alternatively, may include a plurality of chemical reservoirs each including specialized chemical needs. The activation or deactivation of a particular conduit is brought about by computer controlled solenoid valves within the conduit system. This conduit system independently directs the necessary chemicals into the corresponding chemical dispersion conduit. In order to assure that the chemical dispersion conduit and chemical reservoir are not contaminated by waste being removed from the culture vessels, there is no connection between the chemical dispersion conduits and central conduit. The opening to the central conduit is at a safe distance from the chemical dispersion conduit and is always closed during the operation of the chemical dispersion conduit. Additionally, in order to ensure that the chemicals being added to the culture vessel are not inserted too rapidly causing potential turbulence and/or disturbance to the cell culture contained within the culture vessell, the chemicals are directed upon the side of the sterile pipet tip, thereby causing a gentle flow of the chemicals down the side of the sterile pipet tip into the culture vessel. The chemicals added to the particular culture vessels include various biochemicals such as vitamins and similar type nutrients, as well as contaminant free solutions of harvesting chemicals, thereby providing an appropriate environment for the cell cultures contained within the culture vessel. Subsequent to complete processing of the uncovered culture vessel by the nurturing assemblies, the Z assembly is moved such that the cover removers are disposed directly over the culture vessels and the covers may be replaced atop the culture vessel. Once the covers are replaced atop the culture vessels, the Z assembly is moved atop the pipet tip disposal area such that the now used pipet tips may be discarded therein. In order to discard the used pipet tips, the vacuum formed at the pick-up nipple is ceased and rapid vertical movement of the nurturing assembly is provided to assure that the used pipet tips are dislodged and discarded into the pipet tip disposal area. In order to assure the pipet tips have been properly discarded, the nurturing assemblies are once again passed through the infra red beam sensors. Servicing of a new culture vessel proceeds only if the used pipet tips have been properly disposed of.

The disposition and functioning of the Z assembly, with regard to its position above a particular culture vessel, and with regard to the particular servicing performed on the particular culture vessels are directed by the control means of the feeder/harvester assembly. These computer control means control the first, second, and third step motors, the cover removers and the nurturing assemblies, specifically directing the activities undertaken. The specific steps to be ordered by the computer control means are inputted into a computer interface connected to a main computer which stores relevant information regarding all culture vessels and their contents along with feeding and harvesting schedules. Further, the computer control means receives inputs from the vacuum sensor and infra red beam sensors throughout the servidng procedures. Accordingly, the entire procedure is automated and precise, as well as efficient in servicing a large number of culture vessels containing cell cultures therein.

Now that the invention has been described,
What is claimed is:

1. A Cell Feeder/Harvester Assembly for use in combination with and operably controlled by a computer control means for servicing cultures in individual culture vessels comprising:

a primary platform including at least one recessed culture vessel holding area for holding the culture vessels, said primary platform further including at least one sterile pipet tip tray holding recess and at least one pipet tip disposal tray recess, said sterile tip tray holding recess including a pipet tip tray disposed therein, and said pipet tip disposal tray recess including a disposal tray therein, said sterile pipet tip tray being structured to hold a plurality of sterile pipet tips disposed vertically therein, an X assembly movably attached to and extending transversely above said primary platform, said X assembly being structured and disposed to move longitudinally in spaced relation above said primary platform, computer controlled longitudinal drive means controlled by said computer control means and structured and disposed to move said X assembly predetermined longitudinal distances over said primary platform, a Y assembly attached to said X assembly and structured and disposed to move transversely relative to said primary platform in spaced relation thereabove, said Y assembly including a secondary platform mounted thereon, computer controlled transverse drive means controlled by said computer control means and structured and disposed to move said Y assembly predetermined transverse distances over said X assembly and said primary platform, a Z assembly mounted to a top of said secondary platform, said Z assembly being structured and disposed to service a corresponding pair of the culture vessels simultaneously, and including a pair of oppositely disposed cover removers and a pair of oppositely disposed nurturing assemblies, each of said pair of oppositely disposed cover removers being correspondingly disposed adjacent one of said pair of oppositely disposed nurturing assemblies such that a first side of said secondary platform is overhung by a first cover remover and nurturing assembly unit and a second side of said secondary platform is overhung by a second cover remover and nurturing assembly unit, computer controlled vertical drive means controlled by said computer control means and structured and disposed for raising and lowering said cover removers and said nurturing assemblies predetermined vertical distances, said cover removers each including a lower surface structured and disposed to contact and hold a cover of one of said culture vessels for removal and subsequent replacement thereof on said culture vessel, both of said cover removers being structured and disposed to function simultaneously, each of said cover removers including a suction tube extending therethrough to said lower surface thereof, said suction tube being interconnected with an external vacuum source and being structured and disposed to provide sufficient suction at said lower surface of said cover remover so as to remove and hold said cover of said culture vessel when said culture vessel is being serviced, each of said cover removers further including a vacuum sensor structured and disposed to detect successful attachment of said lower surface of said cover remover and said cover of said culture vessel, continued servicing of said culture vessels continuing only if successful attachment is detected for both of said cover removers, said nurturing assemblies each including a central conduit, said nurturing assemblies each further including a pick-up nipple protruding from a lower surface thereof and in fluid flow communication with said central conduit, each of said pick-up nipples being structured and disposed to be simultaneously inserted into a corresponding pipet tip in said sterile pipet tip tray, vacuum means interconnected to each said central conduit through a suction conduit and structured and disposed to provide sufficient suction at said pick-up nipples to secure the pipet tip thereto, means to detect the attachment of a pipet tip to each of said pick-up nipples, continued servicing of said culture vessels proceeding only if attachment of the pipet tip is detected for each of said pick-up nipples, said Z assembly being further structured and disposed to lower the nurturing assemblies and accordingly the pipet tips on each of said pick-up nipples so as to cause each of the respective pipet tips to enter an uncovered one of said culture vessels upon lowering of said nurturing assemblies a computer controlled vertical distance, said vacuum means being further interconnected to said nurturing assemblies through said suction conduit so as to provide suction to remove waste from the uncovered culture vessels through said pipet tips, said suction conduit disposed in fluid flow communication with a waste disposal area, each of said nurturing assemblies further including chemical distributing means structured and disposed to insert necessary chemicals into the uncovered culture vessels, and a chemical distribution conduit disposed in fluid flow communication with said chemical distributing means, said chemical distributing conduit being independent of said central conduit and disposed such that waste passing through said central conduit into said suction conduit does not contaminate said chemical distribution conduit, and said chemical distribution conduit being structured and disposed such that chemicals are directed upon a side of said pipet tip, thereby resulting in a gentle flow down the side of the pipet tip and into one of the culture vessels.

2. A cell feeder/harvester assembly as recited in claim 1 wherein said primary platform includes a first pair of elongate rails extending longitudinally along opposite longitudinal sides thereof, said X assembly being slidably mounted on said first pair of rails.

3. A cell feeder/harvester assembly as recited in claim 2 wherein said computer controlled longitudinal drive means includes a first pair of pulleys disposed adjacent to opposite distal ends of one of said first pair of rails, said first pair of pulleys including a first drive belt drivingly engaged thereabout and drivingly secured to said X assembly such that movement of said first drive belt results in corresponding longitudinal movement of said X assembly relative to said primary platform.

4. A cell feeder/harvester assembly as recited in claim 3 wherein said computer controlled longitudinal drive means further includes a first step motor drivingly connected to said first pair of pulleys so as to rotate said first pair of pulleys, and accordingly move said first drive belt and said X assembly.

5. A cell feeder/harvester assembly as recited in claim 4 wherein said X assembly further includes a second pair of elongate rails extending in spaced, parallel relation above said primary platform in transverse relation thereto, said Y assembly being slidably mounted thereon, said second pair of rails being secured at opposite distal ends thereof to mounting members, said mounting members being structured and disposed to slidably mount said X assembly on said first pair of rails of said primary platform.

6. A cell feeder/harvester assembly as recited in claim 5 wherein said computer controlled transverse drive means includes a second pair of pulleys disposed at opposite distal ends of one of said second pair of rails, said second pair of pulleys having a second drive belt drivingly engaged thereabout and drivingly secured to said Y assembly such that movement of said second drive belt results in corresponding transverse movement of said Y assembly above said primary platform.

7. A cell feeder/harvester assembly as recited in claim 6 wherein said computer controlled transverse drive means further includes a second step motor connected to said second pair of pulleys so as to rotate said second pair of pulleys and accordingly move said second drive belt and said secondary platform as directed by said computer control means.

8. A cell feeder/harvester assembly as recited in claim 7 wherein each chemical distribution conduit of each of said nurturing assemblies is connected to a single chemical supply source, said single chemical supply source having pumping means structured and disposed to distribute precise, predetermined quantities of chemicals into each of said chemical distribution conduits for subsequent dispersion within a corresponding one of said culture vessels.

9. A cell feeder/harvester assembly as recited in claim 8 wherein said computer controlled vertical drive means includes a third pair of pulleys vertically disposed in spaced apart relation from one another between said first cover remover and nurturing assembly unit, and including a fourth pair of pulleys vertically disposed in spaced apart relation from one another between said second cover remover and nurturing assembly unit, said third and said fourth pair of pulleys each including a third drive belt and a fourth drive belt drivingly disposed thereabout respectively, such that rotation of said third and said fourth pair of pulleys results in corresponding movement of said third and said fourth drive belts, said third and said fourth drive belts being correspondingly secured to one of said nurturing assemblies and one of said cover removers such that movement of said third and said fourth drive belts results in upward movement of said cover removers and simultaneously downward movement of said nurturing assemblies.

10. A cell feeder/harvester assembly as recited in claim 9 wherein said computer controlled vertical drive means further includes a third step motor drivingly connected to said third and fourth pairs of pulleys so as to rotate said third and fourth pairs of pulleys, and accordingly move said third and fourth drive belts and said nurturing assemblies and said cover removers, as directed by said computer control means.

11. A cell feeder/harvester assembly as recited in claim 10 further including a computer interface structured and disposed to receive inputs from said computer control means and direct those inputs to said drive means so as to control said first step motor, said second step motor, said third step motor, said cover removers, and said nurturing assemblies.

12. A cell feeder/harvester assembly as recited in claim 10 further including a culture vessel holding tray adapted to be inserted into said recessed culture vessel holding area for holding said culture vessels in a predetermined array.

13. A cell feeder/harvester assembly as recited in claim 12 wherein said means to detect the attachment of one of said pipet tips to each of said pick-up nipples includes a pair of infra red beam sensors through which each of said nurturing assemblies is passed so as to detect the presence of a pipet tip on the respective pick-up nipple.

* * * * *